(12) United States Patent
Arnold et al.

(10) Patent No.: US 11,422,074 B2
(45) Date of Patent: Aug. 23, 2022

(54) LOSSLESS CRYO-GRID PREPARATION STAGE FOR HIGH-RESOLUTION ELECTRON MICROSCOPY

(71) Applicant: UNIVERSITÄT BASEL, Basel (CH)

(72) Inventors: Stefan Alexander Arnold, Basel (CH); Thomas Braun, Munchenstein (CH); Henning Stahlberg, Binningen (CH)

(73) Assignee: UNIVERSITAT BASEL, Basel (CH)

(*) Notice: Subject to any disclaimer, the term of this patent is extended or adjusted under 35 U.S.C. 154(b) by 136 days.

(21) Appl. No.: 15/742,532

(22) PCT Filed: Jul. 6, 2015

(86) PCT No.: PCT/EP2015/065398
§ 371 (c)(1),
(2) Date: Jan. 8, 2018

(87) PCT Pub. No.: WO2017/005297
PCT Pub. Date: Jan. 12, 2017

(65) Prior Publication Data
US 2018/0209881 A1     Jul. 26, 2018

(51) Int. Cl.
*G01N 1/42* (2006.01)
*H01J 37/20* (2006.01)
(Continued)

(52) U.S. Cl.
CPC .............. *G01N 1/42* (2013.01); *H01J 37/20* (2013.01); *A61K 9/127* (2013.01); *B01L 9/06* (2013.01);
(Continued)

(58) Field of Classification Search
CPC .. G01N 1/42; G01N 1/06; G01N 1/04; G01N 1/44; G01N 1/2813; G01N 1/28;
(Continued)

(56) References Cited

U.S. PATENT DOCUMENTS

| 4,753,887 A * | 6/1988 | Bellare | G01N 1/42 435/1.3 |
| 8,754,384 B1 * | 6/2014 | Persoon | H01J 37/20 250/440.11 |

(Continued)

FOREIGN PATENT DOCUMENTS

| CN | 1066923 | 12/1992 |
| CN | 101945617 | 1/2011 |

(Continued)

OTHER PUBLICATIONS

Berriman J et al: "Analysis of transient structures by cryo-microscopy combined with rapid mixing of spray droplets," Ultramicroscopy, vol. 56, No. 4, Dec. 1, 1994, pp. 241-252.

*Primary Examiner* — Benjamin R Whatley
*Assistant Examiner* — Curtis A Thompson
(74) *Attorney, Agent, or Firm* — JMB Davis Ben-David

(57) ABSTRACT

The invention relates to a preparation system and method for preparing a sample for electron microscopy, the preparation system comprising: a liquid handling system (0) comprising a dispensing head (1), wherein said liquid handling system (0) is configured to aspirate and dispense a volume of a sample via the dispensing head (1), a support structure (2) that is configured to accommodate the sample, a temperature-controlled stage (4) that is configured to keep said support structure (2) at a pre-defined temperature, a first adapter (3) configured to hold said support structure (2), and a transfer mechanism (60) that is configured to be connected to the first adapter (3) holding the support structure (2) and to move said support structure (2) into a container (8) containing a liquid cryogen (80) so that the sample on the support structure (2) contacts the cryogen (80).

12 Claims, 4 Drawing Sheets

(51) Int. Cl.

| | |
|---|---|
| G01N 1/28 | (2006.01) |
| H01J 37/26 | (2006.01) |
| G21K 5/10 | (2006.01) |
| G01D 3/00 | (2006.01) |
| G01D 7/00 | (2006.01) |
| A61K 9/127 | (2006.01) |
| C12Q 1/00 | (2006.01) |
| C12M 1/34 | (2006.01) |
| C12Q 1/68 | (2018.01) |
| B01L 9/06 | (2006.01) |
| G01N 1/06 | (2006.01) |
| G01N 1/04 | (2006.01) |
| G01N 1/44 | (2006.01) |

(52) U.S. Cl.
CPC ............... *C12M 1/34* (2013.01); *C12Q 1/00* (2013.01); *C12Q 1/68* (2013.01); *G01D 3/00* (2013.01); *G01D 7/00* (2013.01); *G01N 1/04* (2013.01); *G01N 1/06* (2013.01); *G01N 1/28* (2013.01); *G01N 1/2813* (2013.01); *G01N 1/44* (2013.01); *G21K 5/10* (2013.01); *H01J 37/26* (2013.01); *H01J 37/261* (2013.01); *H01J 2237/002* (2013.01)

(58) Field of Classification Search
CPC ...... H01J 37/20; H01J 37/26; H01J 2237/002; H01J 37/261; B01L 9/06; C12Q 1/00; C12Q 1/68; C12M 1/34; A61K 9/127; G21K 5/10; G01D 3/00; G01D 7/00
See application file for complete search history.

(56) References Cited

U.S. PATENT DOCUMENTS

| | | | |
|---|---|---|---|
| 2003/0152194 A1* | 8/2003 | Nordmeyer | B01L 9/065 378/73 |
| 2005/0107917 A1* | 5/2005 | Smith | B25J 15/0253 700/245 |
| 2006/0068373 A1* | 3/2006 | Bose | G01N 1/42 435/4 |
| 2006/0222694 A1 | 10/2006 | Oh et al. | |
| 2008/0293832 A1* | 11/2008 | Yokoi | G01N 1/42 516/98 |
| 2009/0133410 A1* | 5/2009 | Thorne | G01N 1/42 62/62 |
| 2010/0181495 A1* | 7/2010 | Lihl | G01N 1/42 250/442.11 |
| 2011/0238225 A1 | 9/2011 | Tripathi et al. | |
| 2014/0360286 A1* | 12/2014 | Carragher | H01J 37/261 73/863.11 |
| 2015/0090878 A1 | 4/2015 | Remigy et al. | |

FOREIGN PATENT DOCUMENTS

| | | | | |
|---|---|---|---|---|
| DE | 102011122607 | | 7/2013 | |
| EP | 2381236 | | 10/2011 | |
| EP | 2381236 A1 | * | 10/2011 | ............... G01N 1/42 |
| JP | 2009008657 | | 1/2009 | |
| WO | WO-2013109406 A1 | * | 7/2013 | ........... G01N 1/2813 |

* cited by examiner

LOSSLESS CRYO-GRID PREPARATION STAGE FOR HIGH-RESOLUTION ELECTRON MICROSCOPY

CROSS-REFERENCE TO RELATED APPLICATIONS

This is the U.S. National Stage of International Application No. PCT/EP2015/065398 filed on Jul. 6, 2015.

The invention relates to a preparation system for preparing a sample for electron microscopy and a corresponding method.

In recent years, direct electron detection (DED) cameras for electron microscopes introduced a fast and lasting change to biophysics and structural biology. These cameras now allow the structure determination of large biomolecules by cryo-electron microscopy (cryo-EM) at or close to atomic resolution using a single particle approach (Liao et al., Nature 504, 107-112 (2013); Lu et al. Nature 512, 166-170 (2014)). While image acquisition and processing have largely benefited from the new DED cameras, sample preparation is still in the pre-DED era. Although some degree of automation and control has been introduced by commercial vitrification robots (e.g. Vitrobot, FEI; Leica EM GP, Leica Microsystems), current methods suffer from two major drawbacks: First, a large sample volume (around 3 µl) containing biological sample at high concentration (0.1 mg/ml to 3 mg/ml protein) is required. Second, massive blotting steps removing more than 99% of the sample are employed. Furthermore, the latter directs preferential removal of sample sub-classes leading to an unrepresentative sample population on the EM grid. Not many researchers have attempted to solve these issues. Jain et al. have developed a device, which combines ink-jet picoliter dispensing with a plunge-freezing apparatus (Jain et al., J. Struct. Biol. 179 (1), 68-75 (2012)). This is an interesting approach that effectively decreases the amount of sample consumed per grid. However, ink-jet type dispensing requires a filled sample reservoir from which the droplets can be released. This poses a limitation on the minimal sample volume that needs to be available to fill the reservoir. Some specimens are per se only available in sub-microliter volumes, e.g. lysate from single cells or extracts from microfluidic devices. In addition, some samples are not compatible with ink-jet technology.

Therefore, the problem underlying the present invention is to provide a method, a device and a system allowing a lossless cryo-EM preparation that only consumes minute amounts of sample (few nanoliter) and does not involve any blotting steps.

This problem is solved by a cryo-grid preparation system (also denoted as cryo-grid preparation system) comprising the features of claim 1. Preferred embodiments are stated in the corresponding sub claims and are described below.

According to claim 1, the preparation system for preparing a sample for electron microscopy (EM), particularly transmission EM comprises:
  a (high-precision) liquid handling system comprising a dispensing head, wherein said liquid handling system is configured to aspirate and dispense a volume (preferably as low as 1 nl) of a (e.g. heterogeneous) sample via the inlet/outlet of its dispensing head,
  a support structure that is configured to accommodate the sample,
  a temperature-controlled stage that is configured to keep said support structure at a pre-defined temperature when the support structure is arranged on the temperature-controlled stage (e.g. at a dew point temperature of the environment, e.g. in the vicinity of the support structure, with the possibility of establishing a small offset temperature to induce evaporation/condensation; the dew point is dependent on the ambient air temperature and relative humidity (liquid neither evaporates nor condenses)).
  a first adapter configured to hold said support structure (preferably in a releasable fashion), which first adapter is preferably mounted on said temperature-controlled stage so that the adapter is in thermal contact with the temperature-controlled stage),
  a transfer mechanism (also denoted pick-up/hand-over mechanism or simply hand-over mechanism) that is configured to be connected to the first adapter holding the support structure and to move said support structure into a container containing a liquid cryogen so that the sample on the support structure contacts the cryogen (preferably the cryogen comprises ethane or a mixture of ethane and propane) so that the sample (e.g. liquid film) on the support structure is preferably transformed into a film of amorphous solid water.

Herein a nl (nanoliter) amount or volume are preferably volumes in the range from 1 nl to 100 nl, preferably 1 nl to 10 nl.

According to an embodiment of the invention, the first adapter comprises tweezers for holding the support structure.

According to a preferred embodiment of the invention, the transfer mechanism is configured to pivot the first adapter together with the support structure into a position above the container and to move the adaptor and the support structure downwards after said pivoting so that the sample on the support structure contacts the cryogen in the container.

The support structure may be or comprise a know electron microscopy (EM) grid with a holey carbon film or any other suitable structure.

According to a preferred embodiment of the invention, the system comprises a translation stage assembly that is configured to move the temperature-controlled stage relative to the liquid handling system, such that the dispensing head and the support structure can be brought in close proximity to each other so as to transfer the sample from the liquid handling system to the support structure.

In an embodiment said translation stage assembly may comprise two separate translational stages, wherein one is configured to move the temperature-controlled stage or the support structure in the X- and Y-direction (e.g. horizontal plane), while the other is configured to position the dispensing head (e.g. capillary or microcapillary) in the Z-direction (vertical direction).

Alternatively, in an embodiment, the translation stage assembly may be a XYZ stage assembly, that is configured to position the temperature-controlled stage and support structure with respect to the dispensing head (e.g. capillary or microcapillary) in all dimensions (X,Y and Z).

Regarding the method described further below, said sample transfer can be performed in multiple ways depending on the physical and chemical properties of the sample. (i) Direct deposition and subsequent spreading of a nanoliter volume droplet on the support surface by surface tension effects. (ii) Deposition of a nanoliter volume droplet on the support surface, followed by re-aspiration of sample with a volume smaller than the initially deposited volume. (iii) Deposition of a nanoliter volume droplet on the support structure surface, followed by a relative movement between the support structure and the liquid handling system while the liquid bridge between the two is still established in order to spread the deposited sample on the support structure. (iv) Deposition of a nanoliter volume droplet on the support structure surface in combination with a relative movement of the support structure and the liquid handling system during deposition in order to spread the deposited sample on the support structure.

According to a preferred embodiment of the invention, the system comprises an adjustment means configured to move the first adapter with respect to the temperature-controlled stage so that the support structure can be brought in close contact to the temperature-controlled stage in order to adjust the temperature of the support structure to the proper temperature (e.g. dew point temperature).

According to a preferred embodiment of the invention, the adjustment means comprises a holding means, preferably in the form of an electromagnet, that is configured to releasably hold the first adapter (preferably the tweezers of the first adapter) and preferably to automatically release the first adapter when the sample is positioned on the support structure and preferably comprises a pre-defined temperature.

According to a preferred embodiment of the invention, the transfer mechanism comprises a second adapter, wherein the two adapters are designed to engage with each other when the holding means releases the first adapter (e.g. when releasing the tweezers).

According to a preferred embodiment of the invention, the transfer mechanism is designed to pivot the second adapter above said container when the first adapter is engaged with the second adaptor and released from the holding means.

According to a preferred embodiment of the invention, the transfer mechanism comprises a movement generating means, preferably comprising a solenoid, which movement generating means is configured to move the second adapter downwards when the first adapter and the support structure are positioned above the container, so that the sample on the support structure contacts the cryogen in the container.

According to a preferred embodiment of the invention, the system comprises a means for estimating the film thickness of a sample layer deposited on the support structure, e.g. by IR adsorption, interferometry, or quartz microbalance measurements.

According to a preferred embodiment of the invention, the dispensing head is formed by a capillary, particularly microcapillary, at an end of the liquid handling system, which capillary comprises a tip for accommodating an aspirated sample.

Preferably, an inner diameter of the microcapillary may be within the range from 1 nanometer to 900 micrometer, particularly within the range from 1 nm to 100 micrometer.

According to a preferred embodiment of the invention, the system comprises a first reservoir, into which (in some cases) the dispensing head containing a nanoliter volume of a sample can be immersed so as to allow diffusion-controlled sample conditioning e.g., to exchange the sample buffer, add detergents, or removing problematic substances interfering with electron microscopy. Furthermore, it allows bringing in biological effector molecules or contrast enhancers, such as ammonium molybdate.

According to a preferred embodiment of the invention, the system comprises a second reservoir from which the dispensing head containing a nanoliter volume of sample can aspirate a small volume containing cognitive molecules, e.g., antibodies, binding to target molecules or particles in the sample. These cognitive molecules can be bound to a surface, e.g. of super paramagnetic nanobeads, which can be used as electron dense label, e.g. for diagnostic purposes. This bond can either be a stable chemical bond or forming a photo-cleavable linker. The magnetic property of the assembly allows the trapping of the assembly and bound target molecules by magnetic gradients generated in the dispensing head. After incubation and washing steps, the target molecules can be selectively released by dispensing the sample while the external magnetic field is turned off or after the sample has been illuminated with light of the appropriate wavelength needed to cleave the photo-cleavable linker.

A further aspect of the present invention relates to a method for preparing a sample on a support structure, particularly for transmission electron microscopy, wherein the method particularly used a system according to the invention, and wherein the method comprises the steps of:

providing a support structure on a temperature-controlled stage, and preferably adjusting the temperature of the support structure to the dew point temperature of the environment, to keep the volume of the sample constant, aspirating a pre-defined amount [nl amount] of a sample into a capillary preferably in the form of a microcapillary;

dispensing the sample onto the support structure;

automatically removing the support structure from the temperature-controlled stage, automatically bringing, preferably pivoting, the support structure into a vertical position and inserting the support structure into a liquid cryogen so that the sample is cooled down to an amorphous solid (also denoted as vitrification);

removing the support structure with vitrified sample from the liquid cryogen.

Further features and advantages of the invention shall be described by means of a detailed description of an embodiment with reference to the Figures, wherein FIG. 1 shows a schematic view of the cryo-grid preparation system according to the invention;

Figure 1:
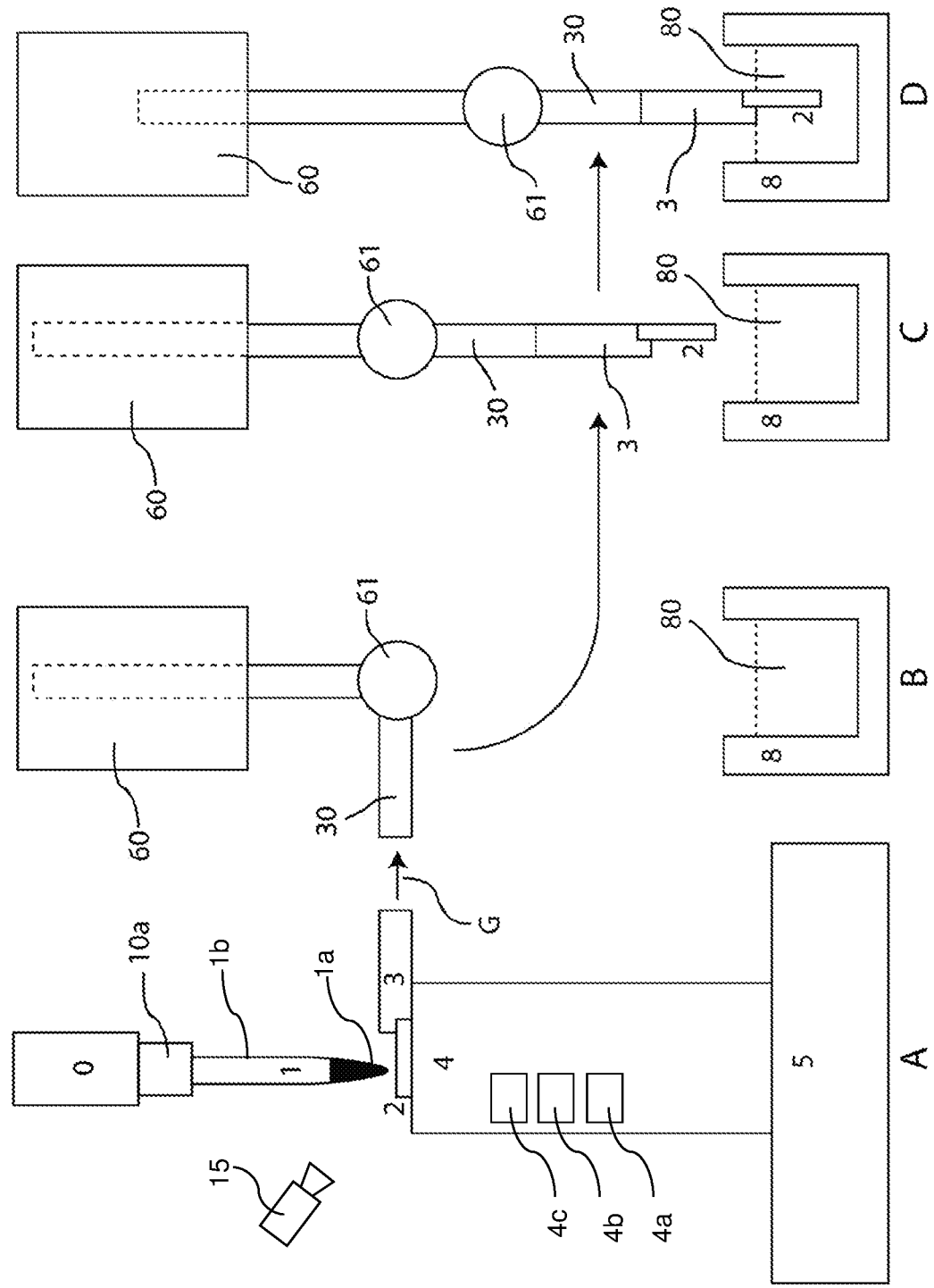

FIG. 1 shows a schematic view of the cryo-grid preparation system according to the invention, which comprises a high precision liquid handling system 0, a dispensing head 1, a support structure 2 (also denoted grid herein); an adapter 3 reversibly holding the support structure 2; a temperature-controlled stage 4; a translation stage 5; a transfer mechanism (pick-up/hand-over mechanism) 60; and a cryogen container 8. The translation stage 5 may be configured to move the stage 4 in all dimensions XY and Z, or only in the dimensions XY. In the latter case a separate Z stage 10*a* is present forming a part of said translation stage, which Z stage 10a is then configured to move the dispensing head 1 in the Z (vertical) direction.

Particularly, the cryo grid preparation is preferably accomplished using the steps: A) Dispensing of a sample onto the support structure 2 (comprising e.g. an EM grid and particularly a holey carbon film arranged on the grid) on the temperature controlled stage 4; B) transfer mechanism 60 grabs adaptor 3 and support structure 2; C) the support structure-holder formed by the adapters 3, 30 swings down and triggers a translation mechanism (D) rapidly transferring the support structure 2 into the cryo agent 80 in container 8.

Figure 2:
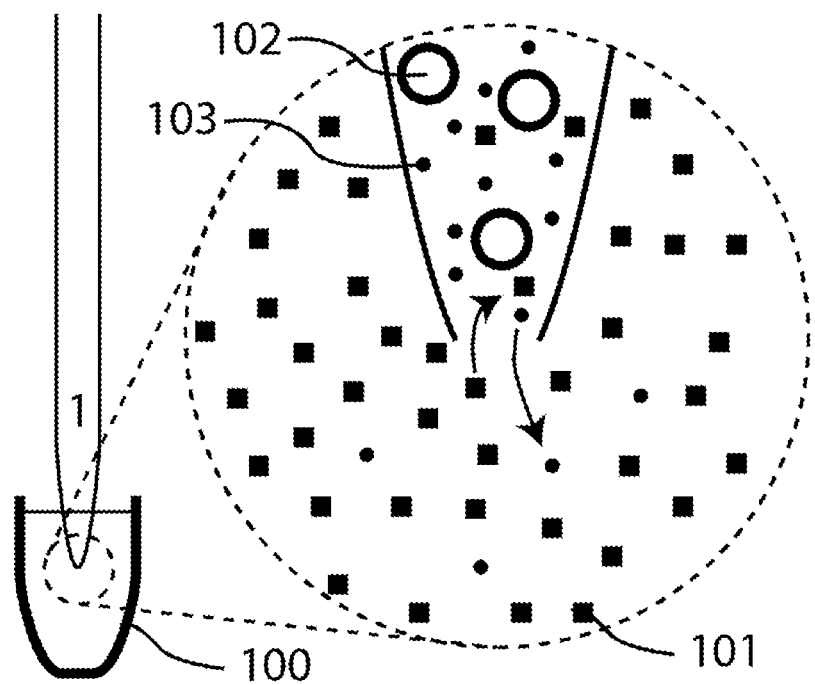
FIG. 2 shows a schematic illustration of the diffusive exchange between molecules in the sample in the dispensing head and molecules in the exchange reservoir.

FIG. 2 shows a schematic illustration of the diffusive exchange between molecules in the sample in the dispensing head and molecules in the exchange reservoir.

Figure 3:
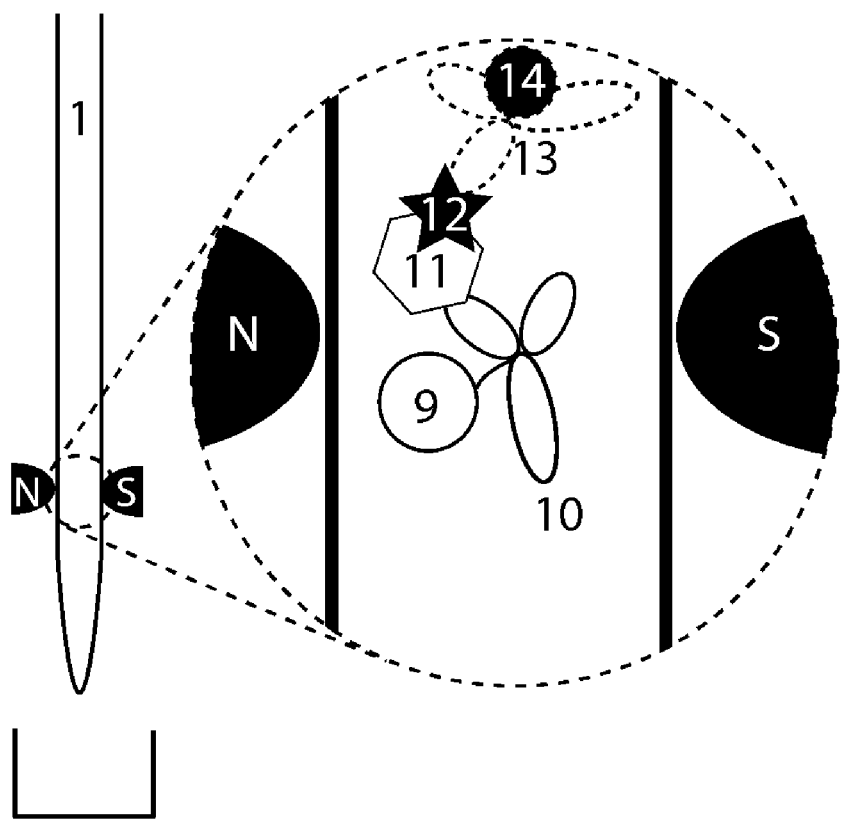
FIG. 3 shows a schematic of miniaturized isolation mechanism for target molecules by cognitive molecules, e.g., antibodies.

FIG. 3 shows a schematic of miniaturized isolation mechanism that may be used in conjunction with the system according to the invention for target molecules by cognitive molecules, e.g., antibodies. Said mechanism comprises magnets building a magnetic trap N,S using a paramagnetic bead 9. FIG. 3 further shows an antibody 10 linked to the paramagnetic bead 9; a Target molecule 11, e.g., protein complex; a binding partner 12 of the target molecule; and a second cognitive molecule 13, e.g., antibody, recognizing the binding partner 12; as well as an electron-dense marker 14 conjugated to second cognitive molecule 13.

Figure 4:
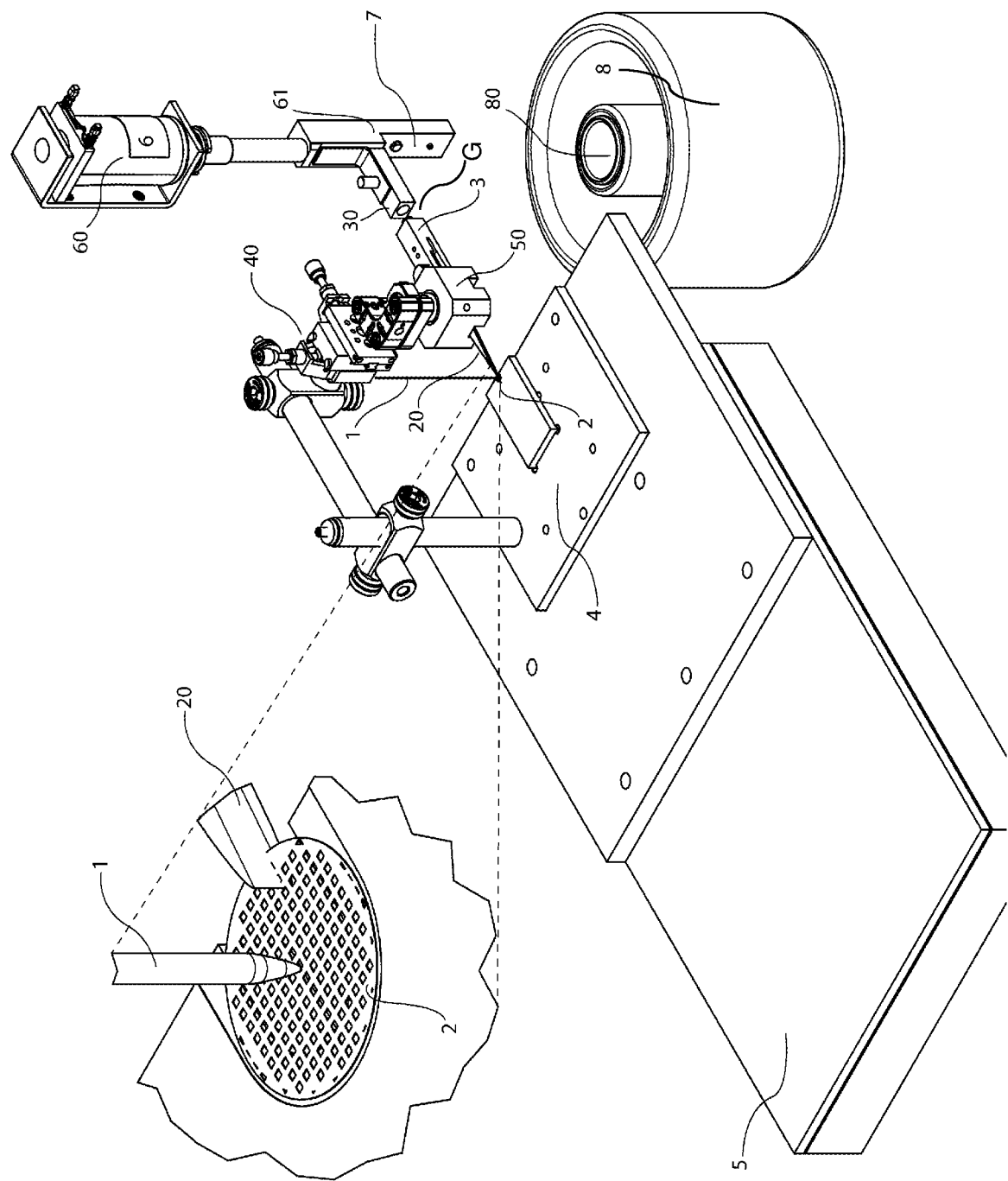
FIG. 4 shows a perspective view of the system according to the invention.

FIG. 4 shows in conjunction with FIG. 1 an embodiment of the system according to the invention. The system comprises, apart from the liquid handling system 0 and the dispensing head 1 formed e.g. by a microcapillary 1b (cf. FIG. 1) a temperature-controlled stage 4; tweezers 20 of an adapter 3 holding a support structure 2 (e.g. an EM grid); an electromagnet 50 holding the tweezers 20; an adjustment means 40, e.g. in the form of an xyz manual alignment, to ensure a flat positioning of the EM grid on the temperature-controlled stage 4, wherein said adjustment means 40 is mounted on the temperature-controlled stage 4; a first adapter 3 mounted on the tweezers 20 with a screw to open and close the tweezers 20 of adapter 3, separated by a gap G from a second adapter 30 on the transfer mechanism 60 (also denoted as injector assembly). Two attracting Nd magnets are inserted into the ends of the adapters 3, 30, a third Nd magnet is holding the second adapter 30 in a horizontal position as shown in FIG. 4. The system/transfer mechanism 60 further comprises a solenoid 6 with e.g. 30 mm hub; a secondary circuit switch 7 that is closed when the tweezers 20 are hitting the switch, which triggers the solenoid 6 and moves the EM grid 2 downwards into the cryogen 80 contained in container 8.

In detail, the liquid handling system 0 consists of a high-precision syringe pump connected to a fused silica microcapillary 1b forming the dispensing head 1. Both are completely filled with system liquid (e.g. water). The syringe pump is able to aspirate and dispense volumes as low as 1 nl of heterogeneous sample (e.g. 20S Proteasome, tobacco-mosaic virus, liposomes) via the free end of its microcapillary tip 1a.

The sample can be aspirated in direct contact with the system liquid, or a small air plug of a few nanoliter can be aspirated before sample aspiration to effectively separate sample and system liquid.

The microcapillary tip 1a can be straight or tapered to a specific inner diameter. Here a 250 μm inner diameter microcapillary 1b with a tapered tip of 40 μm inner diameter was used.

The microcapillary tip 1a containing the sample can be immersed into a first reservoir 100, e.g. an Eppendorf tube, allowing diffusion-controlled exchange of salt ions 103 from the sample into the first reservoir 100 as shown in FIG. 2. Large molecules or proteins 102 exhibit smaller diffusion constants and are not lost during incubation time. Other small molecules 101, such as biological effector molecules or contrast enhancers, e.g., ammonium molybdate, can diffuse into the sample contained in the microcapillary 1b. This exchange can be enhanced by bringing the sample in direct contact with the system liquid ($H_2O$ in this case) during aspiration (no air gap between sample and system liquid).

Generally, in all embodiments, the temperature-controlled stage 4 may comprise a water-cooled peltier element 4a controlled by a peltier controller 4b. The peltier controller 4b gets the stage temperature from a temperature sensor 4c mounted on the stage 4. The actual dew point temperature is delivered by a dew point sensor that measures both ambient temperature and relative humidity inside the experimental chamber and continuously calculates the dew point temperature, which is fed back into the peltier controller via control software. Through the control software it is possible to add a small temperature offset to increase evaporation or condensation.

A support structure 2 in the form of an EM grid with a holey carbon film is held by small tweezers 20 of adapter 3. The tweezers 20 are securely mounted in said first adapter 3 by e.g. two screws. An e.g. third screw allows the opening and closing of the tweezers 20 by applying pressure on them. The back end of this first adapter 3 has a Neodymium magnet inserted.

The support structure 2, tweezers 20, and first adapter 3 form an assembly. This assembly is held in a horizontal position by a holding means in the form of e.g. said electromagnet 50 that is in contact with the tweezers 20. The electromagnet 50 itself is mounted to said adjustment means 40 that allows manual alignment in all dimensions in order to align the support structure/grid 2 perfectly with the temperature-controlled stage 4, where the support structure/grid 2 has to lie flat for good thermal contact and effective sample deposition.

A translation stage assembly 5 (cf. e.g. FIG. 1) comprising e.g. a combination of multiple motorized linear stages enables the precise positioning of the microcapillary tip 1a above the support structure's 2 surface on the temperature-controlled stage 4. The dispensing head 1 and surface of the grid 2 are brought in close proximity to transfer the sample from the microcapillary tip 1a to the support structure (e.g. grid) 2.

Particularly, while the adjustment means 40 is mounted on the temperature controlled stage 4, the microcapillary 1b is not connected to the temperature controlled stage 4 such that the latter can by moved by the stage assembly 5 with respect to the microcapillary 1b which may be held by a suitable holding means not indicated in FIG. 4. Particularly, said microcapillary 1b (dispensing head 1) is mounted on a separate Z-axis stage 10a (cf. FIG. 1) that allows the adjustment of the vertical position of the microcapillary 1b with respect to the support structure 2. Particularly, the stage assembly 5 allows to automatically move the temperature-controlled stage in the XY plane along which the stage 4 extends.

Said sample transfer can be performed in multiple ways depending on the physical and chemical properties of the sample. (i) Direct deposition and subsequent spreading of a nanoliter volume droplet on the support structure 2 (e.g. EM grid) by surface tension effects. (ii) Deposition of a nanoliter volume droplet on the support structure 2 (e.g. EM grid), followed by re-aspiration of sample with a volume smaller than the initially deposited volume. (iii) Deposition of a nanoliter volume droplet on the support structure 2 (e.g. EM grid), followed by a relative movement between the EM grid and the microcapillary tip 1a while the liquid bridge between the two is still established in order to spread the deposited sample on the EM grid. (iv) Deposition of a nanoliter volume droplet on the support structure 2 (e.g. EM grid) in combination with a relative movement of the support structure 2 (e.g. EM grid) and microcapillary tip 1a during deposition in order to spread the deposited sample on the support structure 2.

Preferably, the film thickness is estimated by visual inspection via a camera 15, which can be arranged in any location that is suitable for inspecting said thickness.

The transfer mechanism (hand-over mechanism) 60 comprises a second adapter 30 that also has a Neodymium magnet inserted on one end, and is connected via a rotating hinge 61 with a large solenoid 6 on the other end. To keep this second adapter 30 in a horizontal position, a third Neodymium magnet is placed accordingly. The first and second adapter 3, 30 are separated by a small gap G. The two inserted Neodymium attract each other, joining of the two however is hindered by the electromagnet 50 holding firmly to the assembly 2, 20, 3 (e.g. the tweezers 20).

After sample deposition, a rapid injection of the EM grid into cryogenic liquid 80, usually ethane or a mixture of ethane/propane (40/60), has to occur. This is performed by turning off the electromagnet (software controlled) 50, which enables the two adapters 3, 30 to snap together and form a new, heavier assembly. This new assembly is too heavy to be held in the original position by the third Neodymium magnet. It quickly falls, due to an action of gravity, into the vertical position (hinge 61 on the other side of second adapter 30). If it reaches the vertical position, it is held in place by another magnet to prevent it from bouncing back and forth. At the same time, an electrical circuit is closed through the metallic part of the falling assembly (e.g. switch 7). This triggers a secondary circuit that controls the solenoid controller. As a result, the solenoid 6 is activated and a 30 mm hub is shot downwards, finally injecting the support structure (e.g. EM grid) 2 into the cryogen 80 in the container 8. The whole process from turning on the solenoid 6 until the support structure 2 is shot into the cryogen 80 occurs within one third of a second time and enables the vitrification of the deposited liquid film.

EXAMPLE

Imaging of a Sample Prepared According to the Invention

Cryo-grids were prepared with the system shown in FIGS. 1 and 4.

Figure 5:
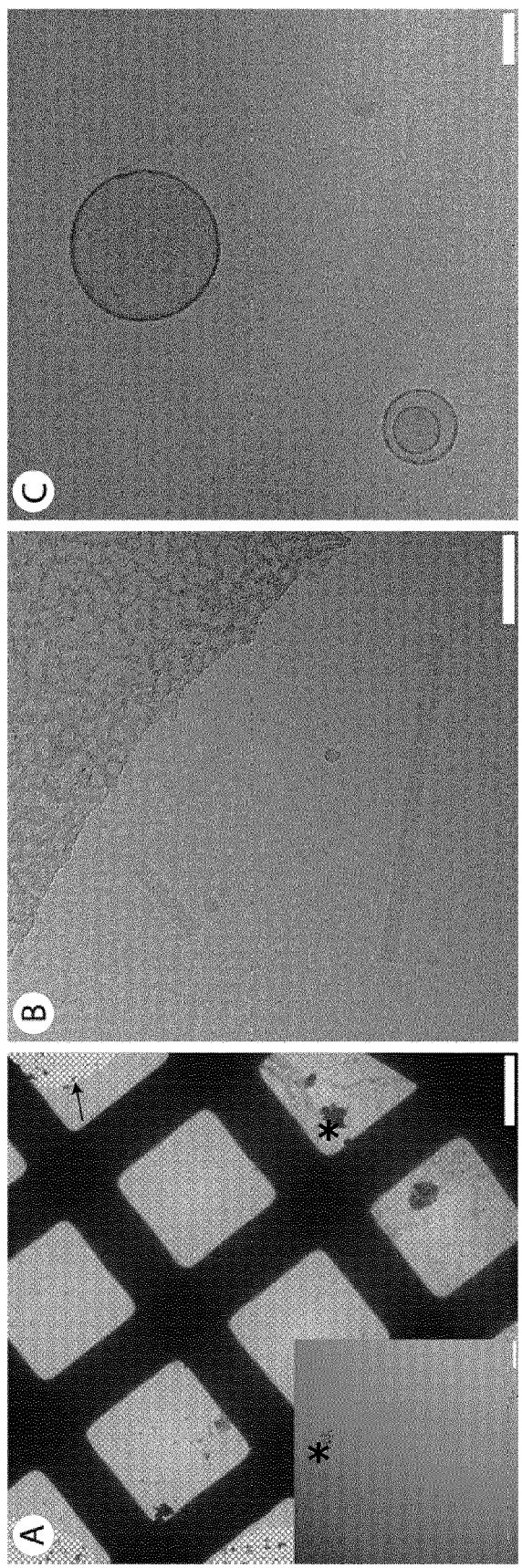
FIG. 5A shows an overview of a cryo-grid prepared with the system shown in FIGS. 1 and 4 showing a 5 nl droplet dispensed on a holey carbon film.
FIG. 5B shows a higher magnification cryo-EM image of Tobacco Mosaic Virus (TMV) embedded in amorphous buffer.
FIG. 5C shows a higher magnification cryo-EM image of PDMS-based vesicles embedded in amorphous buffer.

FIG. 5A shows an overview cryo-EM image showing a 5 nl droplet dispensed on a holey carbon film. Note the homogeneous amorphous water layer. The black arrow indicates the periphery of the dispensed buffer. The scale bar is 50 µm. The inset shows a higher magnification view of the amorphous buffer (PBS) in a hole. The black spots denoted by "*" likely originate from the aluminum surface supporting the EM grid during glow-discharge treatment prior to sample deposition. The scale bar of the inset is 80 nm.

FIG. 5B shows a higher magnification cryo-EM image of Tobacco Mosaic Virus (TMV) embedded in vitreous ice. Scale bar is 80 nm.

FIG. 5C shows a higher magnification cryo-EM image of PDMS-based vesicles embedded in amorphous buffer. The scale bar is 80 nm. The amorphous solid layer of the buffer is homogeneous and mostly free of contamination.

The invention claimed is:

1. A preparation system for preparing a sample for electron microscopy, comprising:
    a liquid handling system (0) comprising a dispensing head (1), wherein said liquid handling system (0) is configured to aspirate and dispense a volume of the sample via the dispensing head (1),
    a support structure (2) that is configured to accommodate the sample,
    a temperature-controlled stage (4) comprising a peltier element (4a), a peltier controller (4b) controlling the peltier element and a temperature sensor (4c) mounted on the temperature-controlled stage to keep said support structure (2) at a pre-defined temperature, the temperature-controlled stage comprising a surface to allow positioning of the support structure on the surface of the temperature-controlled stage to provide thermal contact between the support structure and the temperature-controlled stage,
    a first adapter (3) configured to hold said support structure (2),
    a transfer mechanism (60) that is configured to be connected via a second adapter (30) of the transfer mechanism (60) to the first adapter (3) holding the support structure (2), wherein the transfer mechanism (60) comprises a hinge (61) to pivot an assembly comprising the first and the second adapter (3, 30) and the support structure (2) from a horizontal position into a vertical position above a container (8), and wherein the transfer mechanism (60) comprises a switch (7) that is closed by the assembly in the vertical position activating the transfer mechanism to move the assembly (3, 30, 2) downwards after said pivoting so that the sample on the support structure (2) contacts a liquid cryogen (80) in the container (8), and
    a translation stage assembly (5) comprising multiple motorized linear stages configured to move the temperature-controlled stage (4) relative to the liquid handling system (0), such that the dispensing head (1) and the support structure (2) can be brought in close proximity to each other so as to transfer the sample from the liquid handling system (0) to the support structure (2).

2. The preparation system according to claim 1, characterized in that the preparation system comprises an adjustment means (40) configured to hold the first adapter (3) with respect to the temperature-controlled stage (4) in an adjustable manner.

3. The preparation system according to claim 2, characterized in that the adjustment means (40) comprises a holding means (50) that is configured to releasably hold the first adapter (3).

4. The preparation system according to claim 1, characterized in that the transfer mechanism (60) comprises a movement generating means that is configured to move the assembly comprising the second adapter (30), the first adapter and the support structure downwards when the assembly is positioned above the container (8) in said vertical position, so that the sample on the support structure (2) contacts the cryogen (80) in the container (8).

5. The preparation system according to claim 1, characterized in that the preparation system comprises a means (15) for estimating a film thickness of the sample layer deposited on the support structure.

6. The preparation system according to claim 1, characterized in that the dispensing head (1) is formed by a capillary (1b) at an end of the liquid handling system (0), which capillary comprises a tip for accommodating the sample.

7. The preparation system according to claim 1, characterized in that the preparation system comprises a first reservoir (100), into which the dispensing head (1) containing a nanoliter volume of the sample can be immersed.

8. The preparation system according to claim 1, characterized in that the preparation system comprises a reservoir from which the dispensing head (1) containing a nanoliter volume of the sample can aspirate a volume containing cognitive molecules.

9. The preparation system according to claim 3, characterized in that the holding means is formed as an electromagnet (50).

10. The preparation system according to claim 4, characterized in that the movement generating means comprises a solenoid (6).

11. The preparation system according to claim 6, characterized in that the capillary is a microcapillary (1b).

12. A preparation system for preparing a sample for electron microscopy, comprising:
  a liquid handling system (0) comprising a dispensing head (1), wherein said liquid handling system (0) is configured to aspirate and dispense a volume of the sample via the dispensing head (1),
  a support structure (2) that is configured to accommodate the sample,
  a stage (4) configured to place the support structure thereon such that the support structure is in thermal contact with the stage (4),
  a first adapter (3) configured to hold said support structure (2),
  a transfer mechanism (60) that is configured to be connected to the first adapter (3) holding the support structure (2) and to move said support structure (2) into a container (8) containing a liquid cryogen (80) so that the sample on the support structure (2) contacts the cryogen (80), wherein the transfer mechanism (60) comprises a hinge configured to let the first adapter (3) together with the support structure (2) fall under the action of gravity in a pivoting motion from a horizontal position into a vertical position above the container (8), and wherein the transfer mechanism (60) is configured to move the first adapter (3) and the support structure (2) downwards after said pivoting so that the sample on the support structure (2) contacts the cryogen (80) in the container (8).

* * * * *